United States Patent
Corl

(10) Patent No.: US 10,123,775 B2
(45) Date of Patent: Nov. 13, 2018

(54) TRANSDUCER WITH PROTECTIVE LAYER AND ASSOCIATED DEVICES, SYSTEMS, AND METHODS

(71) Applicant: Volcano Corporation, San Diego, CA (US)

(72) Inventor: Paul Douglas Corl, Palo Alto, CA (US)

(73) Assignee: Volcano Corporation, San Diego, CA (US)

( * ) Notice: Subject to any disclaimer, the term of this patent is extended or adjusted under 35 U.S.C. 154(b) by 486 days.

(21) Appl. No.: 14/212,707

(22) Filed: Mar. 14, 2014

(65) Prior Publication Data

US 2014/0276087 A1 Sep. 18, 2014

Related U.S. Application Data

(60) Provisional application No. 61/781,159, filed on Mar. 14, 2013.

(51) Int. Cl.
*A61B 8/12* (2006.01)
*A61B 8/00* (2006.01)
(Continued)

(52) U.S. Cl.
CPC .............. *A61B 8/4494* (2013.01); *A61B 8/12* (2013.01); *B06B 1/0292* (2013.01);
(Continued)

(58) Field of Classification Search
None
See application file for complete search history.

(56) References Cited

U.S. PATENT DOCUMENTS 5,160,870 A * 11/1992 Carson .................. B06B 1/0629
310/324
5,488,954 A * 2/1996 Sleva .................... B06B 1/0692
600/463

(Continued)

FOREIGN PATENT DOCUMENTS

| JP | 2008-093214 | 4/2008 |
|---|---|---|
| JP | 2012151583 A | 8/2012 |
| KR | 10-2007-0045898 | 5/2007 |

OTHER PUBLICATIONS

International Search Report and Written Opinion received in corresponding Patent Cooperation Treaty Application No. PCT/US2014/028552, dated Jun. 26, 2014, 15 pages.

*Primary Examiner* — Mark Remaly

(57) ABSTRACT

A method of fabricating miniature ultrasound transducers includes receiving a wafer on which a plurality of miniature ultrasound transducers is formed. The miniature ultrasound transducers each includes: a transducer membrane that contains a piezoelectric material and a first bond pad and a second bond pad each electrically coupled to the transducer membrane. A protective layer is conformally deposited over the plurality of miniature ultrasound transducers from a front side of the wafer. A first etching process is performed to form a plurality of first trenches that extend into the wafer from the front side. The first trenches are etched through the protective layer. The first trenches are disposed between adjacent miniature ultrasound transducers. A second etching process is performed to remove portions of the protective layer disposed over the first and second bond pads, thereby exposing the first and second bond pads.

19 Claims, 11 Drawing Sheets

(51) Int. Cl.
*H01L 41/332* (2013.01)
*H01L 41/09* (2006.01)
*H01L 41/23* (2013.01)
*B06B 1/02* (2006.01)
*B06B 1/06* (2006.01)
*H01L 41/053* (2006.01)

(52) U.S. Cl.
CPC ........ *B06B 1/0629* (2013.01); *H01L 41/0533* (2013.01); *H01L 41/098* (2013.01); *H01L 41/23* (2013.01); *H01L 41/332* (2013.01)

(56) References Cited

U.S. PATENT DOCUMENTS

| | | | |
|---|---|---|---|
| 6,331,163 B1* | 12/2001 | Kaplan | A61B 5/0031 600/373 |
| 6,641,540 B2* | 11/2003 | Fleischman | B06B 1/0688 600/459 |
| 7,008,812 B1* | 3/2006 | Carley | B81B 7/0077 438/52 |
| 7,331,236 B2* | 2/2008 | Smith | B60C 23/0408 73/703 |
| 7,415,883 B2* | 8/2008 | Kaplan | A61B 5/00 73/570 |
| 2003/0114760 A1* | 6/2003 | Robinson | B06B 1/0685 600/459 |
| 2003/0205947 A1 | 11/2003 | Klee et al. | |
| 2005/0177045 A1* | 8/2005 | Degertekin | G01N 29/2406 600/457 |
| 2005/0200241 A1 | 9/2005 | Degertekin | |
| 2010/0168583 A1* | 7/2010 | Dausch | A61B 8/12 600/466 |
| 2011/0090289 A1 | 4/2011 | Mizukami | |
| 2011/0198970 A1* | 8/2011 | Martin | B81B 7/0058 310/340 |
| 2012/0206014 A1 | 8/2012 | Bibl et al. | |
| 2015/0165479 A1* | 6/2015 | Lasiter | B06B 1/0666 310/322 |
| 2015/0276685 A1* | 10/2015 | Yasuhara | A61B 8/12 73/632 |

* cited by examiner

TRANSDUCER WITH PROTECTIVE LAYER AND ASSOCIATED DEVICES, SYSTEMS, AND METHODS

PRIORITY DATA

This application is a utility application of Provisional Patent Application No. 61/781,159, filed Mar. 14, 2013, and entitled "Wafer-Scale Transducer Coating and Method," the disclosure of which is hereby incorporated by reference in its entirety.

TECHNICAL FIELD

The present disclosure relates generally to intravascular ultrasound (IVUS) imaging, and in particular, to a wafer level coating of a protective layer to a plurality of ultrasound transducers to be used in an IVUS catheter for IVUS imaging.

BACKGROUND

Intravascular ultrasound (IVUS) imaging is widely used in interventional cardiology as a diagnostic tool for assessing a vessel, such as an artery, within the human body to determine the need for treatment, to guide intervention, and/or to assess its effectiveness. An IVUS imaging system uses ultrasound echoes to form a cross-sectional image of the vessel of interest. Typically, IVUS imaging uses a transducer on an IVUS catheter that both emits ultrasound signals (waves) and receives the reflected ultrasound signals. The emitted ultrasound signals (often referred to as ultrasound pulses) pass easily through most tissues and blood, but they are partially reflected at impedance discontinuities arising from tissue structures (such as the various layers of the vessel wall), red blood cells, and other features of interest. The IVUS imaging system, which is connected to the IVUS catheter by way of a patient interface module, processes the received ultrasound signals (often referred to as ultrasound echoes) to produce a cross-sectional image of the vessel where the IVUS catheter is located.

One preferred type of ultrasound transducer for IVUS imaging is the piezoelectric micromachined ultrasound transducer (PMUT), which is a microelectromechanical system (MEMS) device, typically fabricated in large batches on a silicon wafer substrate. MEMS fabrication techniques are used to produce thousands of PMUTs on a single silicon wafer. Typically, a PMUT may be formed by depositing a piezoelectric polymer onto a micro-machined silicon substrate. The silicon substrate may also include electronic circuitry used to provide an electrical interface to the transducer. Alternatively, the electronic circuitry associated with the PMUT may be contained in a separate application-specific integrated circuit (ASIC) which is located in close proximity to the PMUT device and connected by electrical leads. The PMUT MEMS device with its associated electronic circuit (either included on the same substrate or located on a separate adjacent ASIC), with an attached length of electrical cable is referred to as a tadpole assembly based on its configuration consisting of a somewhat bulbous transducer assembly coupled to a long tail-like electrical cable. Currently, PMUT tadpole assemblies are coated with Parylene to insulate the front electrode and other electrical connections from contact with fluids (e.g., saline or blood). This is inconvenient, since it is complicated to introduce a large number of tadpole assemblies into the Parylene chamber and to protect the attached electrical cables from being coated.

Therefore, while conventional wafer fabrication techniques and methods of coating a protective layer on transducer assemblies at the tadpole stage are generally adequate for their intended purposes, they have not been entirely satisfactory in every aspect.

SUMMARY

Intravascular ultrasound (IVUS) imaging is used to help assess medical conditions inside a human body. The IVUS catheter may include a piezoelectric micromachined ultrasound transducer PMUT. As a part of its operation, an ultrasound transducer has electrodes that are used to apply electrical signals to the transducer. To protect the transducers from fluids and to insulate the electrical signals from the surrounding medium such as blood or saline, a protective coating may be formed on the front side of the transducer during the wafer fabrication process, rather than at the later tadpole assembly stage. This protective coating may include a Parylene material, which is deposited using a chemical vapor deposition process.

The present disclosure provides various embodiments of an ultrasound transducer for use in intravascular ultrasound (IVUS) imaging. An exemplary ultrasound transducer is a piezoelectric micromachined ultrasound transducer, fabricated on a wafer substrate (typically a silicon wafer). This exemplary transducer includes a substrate having a first side and a second side opposite the first side. A transducer membrane is disposed on the first side of the substrate. The transducer membrane contains a piezoelectric layer. A protective layer is conformally disposed over the transducer membrane, but not over the second side of the substrate. A well is disposed in the second side of the substrate, extending substantially through the substrate, aligned to the transducer membrane, and terminating at the back side of the transducer membrane.

An exemplary ultrasound transducer includes a substrate having a first side and a second side opposite the first side. A well is disposed in the substrate. The well is filled with a backing material. A transducer membrane is disposed on the first side of the substrate. The transducer membrane contains a piezoelectric layer. A first conductive layer is disposed over the transducer membrane. A second conductive layer is disposed below the transducer membrane. A first bond pad is disposed on the first conductive layer. A second bond pad is disposed on the second conductive layer. A protective layer is disposed over the transducer membrane and over the first and second conductive layers. The protective layer contains recesses that expose the first and second bond pads. A well is disposed in the second side of the substrate, extending substantially through the substrate, aligned to the transducer membrane, and terminating at the back side of the transducer membrane.

The present disclosure further provides a method of fabricating miniature ultrasound transducers. The method includes receiving a wafer on which a plurality of miniature ultrasound transducers is formed. The miniature ultrasound transducers each include: a transducer membrane that contains a piezoelectric material, a first bond pad, and a second bond pad, each electrically coupled to the transducer membrane. A protective layer is conformally deposited over the plurality of miniature ultrasound transducers from a front side of the wafer. A first etching process is performed to form a plurality of first trenches that extend into the wafer from the front side. The first trenches are etched through the protective layer and deeply into the substrate, and the first trenches are disposed between adjacent miniature ultrasound transducers. A second etching process is performed to remove portions of the protective layer disposed over the first and second bond pads, thereby exposing the first and second bond pads.

Both the foregoing general description and the following detailed description are exemplary and explanatory in nature and are intended to provide an understanding of the present disclosure without limiting the scope of the present disclosure. In that regard, additional aspects, features, and advantages of the present disclosure will become apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
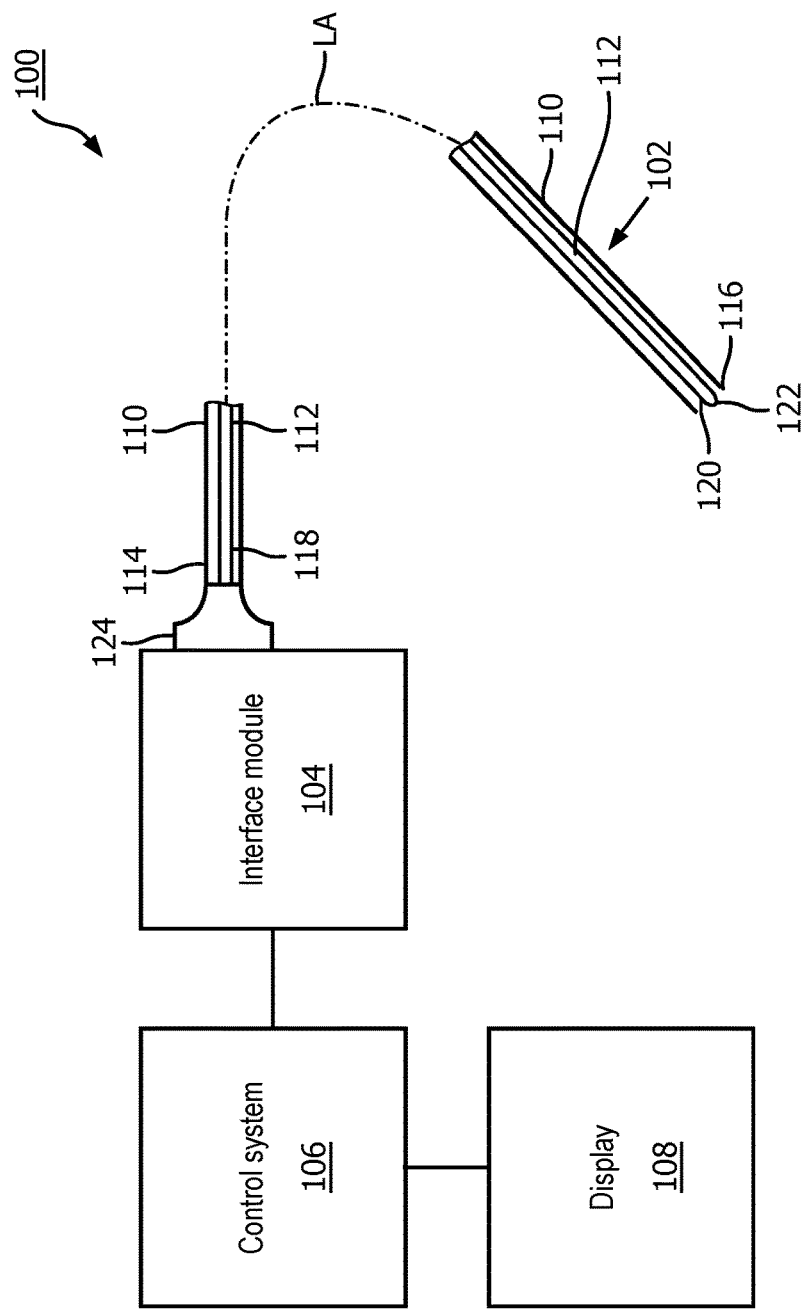
FIG. 1 is a schematic illustration of an intravascular ultrasound (IVUS) imaging system according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, the present disclosure provides an ultrasound imaging system described in terms of cardiovascular imaging, however, it is understood that such description is not intended to be limited to this application. In some embodiments, the ultrasound imaging system includes an intravascular imaging system. The imaging system is equally well suited to any application requiring imaging within a small cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

There are two types of IVUS catheters in common use today: solid-state and rotational. An exemplary solid-state IVUS catheter uses an array of transducers (typically 64) distributed around a circumference of the catheter and connected to an electronic circuit. The circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the imaging system with a simple electrical cable and a standard detachable electrical connector.

An exemplary rotational IVUS catheter includes a single ultrasound transducer located at a tip of a flexible driveshaft that spins inside a sheath inserted into the vessel of interest. The transducer is typically oriented such that the ultrasound signals propagate generally perpendicular to an axis of the catheter. In the typical rotational IVUS catheter, a fluid-filled (e.g., saline-filled) sheath protects the vessel tissue from the spinning transducer and flexible driveshaft while permitting ultrasound signals to freely propagate from the transducer into the tissue and back. As the driveshaft rotates (for example, at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the driveshaft. The same transducer then listens for returning ultrasound signals reflected from various tissue structures, and the imaging system assembles a two dimensional image of the vessel cross-section from a sequence of several hundred of these ultrasound pulse/echo acquisition sequences occurring during a single revolution of the transducer.

FIG. 1 is a schematic illustration of an IVUS imaging system 100 according to various aspects of the present disclosure. The IVUS imaging system 100 includes an IVUS catheter 102 coupled via a patient interface module (PIM) 104 to an IVUS control system 106. The control system 106 is coupled to a monitor 108 that displays an IVUS image, such as an image generated by the IVUS system 100.

In some embodiments, the IVUS catheter 102 is a rotational IVUS catheter, which may be similar to a Revolution® Rotational IVUS Imaging Catheter available from Volcano Corporation and/or rotational IVUS catheters disclosed in U.S. Pat. No. 5,243,988 and U.S. Pat. No. 5,546,948, both of which are incorporated herein by reference in their entirety. The catheter 102 includes an elongated, flexible catheter sheath 110 (having a proximal end portion 114 and a distal end portion 116) shaped and configured for insertion into a lumen of a blood vessel (not shown). A longitudinal axis LA of the catheter 102 extends between the proximal end portion 114 and the distal end portion 116. The catheter 102 is flexible such that it can adapt to the curvature of the blood vessel during use. In that regard, the curved configuration illustrated in FIG. 1 is for exemplary purposes and in no way limits the manner in which the catheter 102 may curve in other embodiments. Generally, the catheter 102 may be configured to take on any desired straight or arcuate profile when in use.

A rotating imaging core 112 extends within the sheath 110. The imaging core 112 has a proximal end portion 118 disposed within the proximal end portion 114 of the sheath 110 and a distal end portion 120 disposed within the distal end portion 116 of the sheath 110. The distal end portion 116 of the sheath 110 and the distal end portion 120 of the imaging core 112 are inserted into the vessel of interest during operation of the IVUS imaging system 100. The usable length of the catheter 102 (for example, the portion that can be inserted into a patient, specifically the vessel of interest) can be any suitable length and can be varied depending upon the application. The proximal end portion 114 of the sheath 110 and the proximal end portion 118 of the imaging core 112 are connected to the interface module 104. The proximal end portions 114, 118 are fitted with a catheter hub 124 that is removably connected to the patient interface module 104. The catheter hub 124 facilitates and supports a rotational interface that provides electrical and mechanical coupling between the catheter 102 and the patient interface module 104.

The distal end portion 120 of the imaging core 112 includes a transducer assembly 122. The imaging core 112 is configured to be rotated (either by use of a motor or other rotary device) to obtain images of the vessel. The transducer assembly 122 can be of any suitable type for visualizing a vessel and, in particular, a stenosis in a vessel. In the depicted embodiment, the transducer assembly 122 includes a piezoelectric micromachined ultrasonic transducer (PMUT) and associated circuitry, such as an application-specific integrated circuit (ASIC). An exemplary PMUT used in IVUS catheters may include a polymer piezoelectric membrane, such as that disclosed in U.S. Pat. No. 6,641,540, hereby incorporated by reference in its entirety. The PMUT transducer can provide greater than 100% bandwidth for optimum resolution in a radial direction, and a spherically-focused aperture for optimum azimuthal and elevation resolution. The transducer assembly 122 may also include a housing having the PMUT transducer and associated circuitry disposed therein, where the housing has an opening through which ultrasound signals generated by the PMUT may travel. Alternatively, the transducer assembly 122 includes a capacitive micromachined ultrasonic transducer (CMUT).

Figure 2:
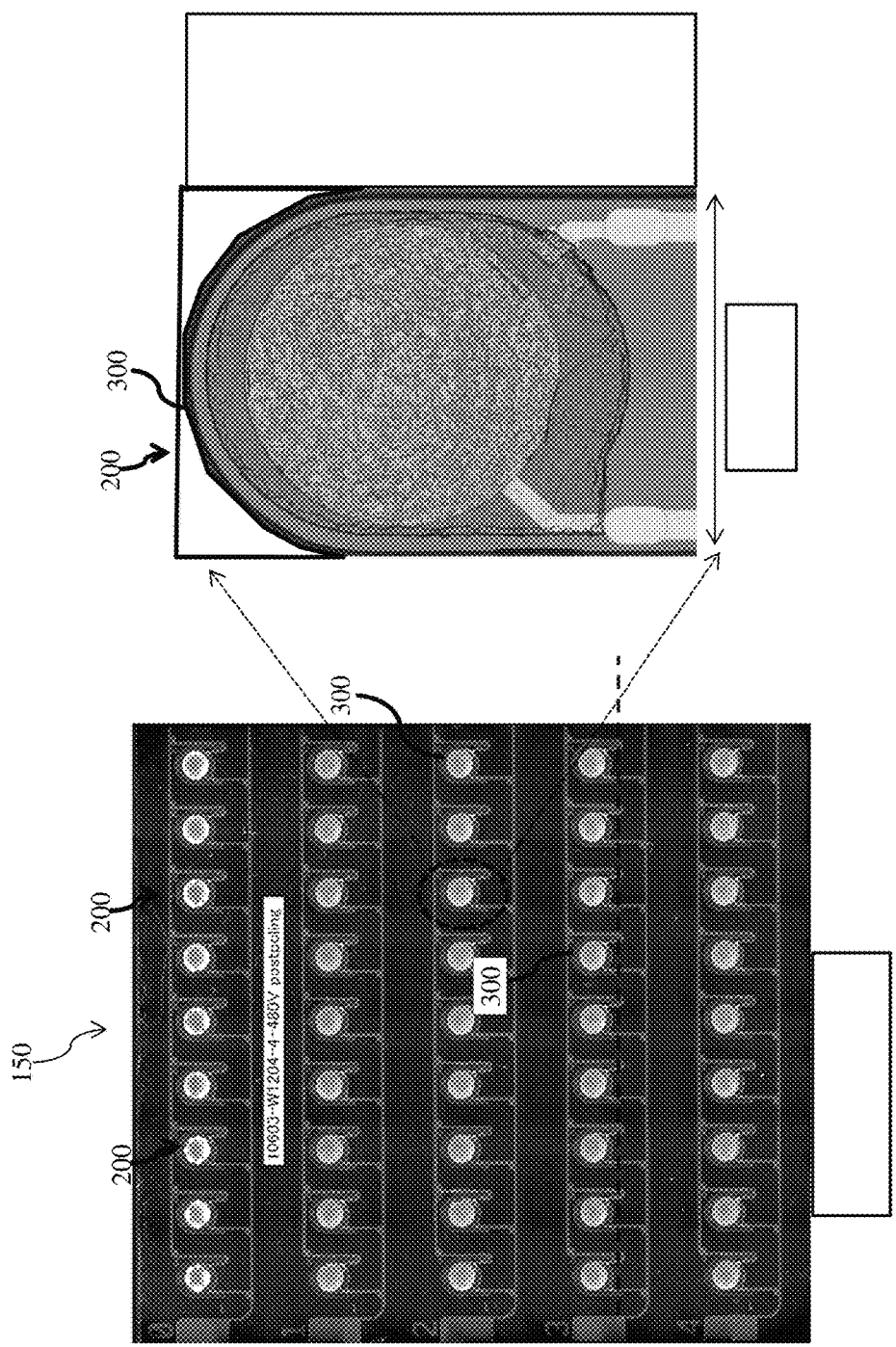
FIG. 2 is a diagrammatic top view of a portion of a wafer containing a plurality of transducers according to various aspects of the present disclosure.

FIG. 2 is a simplified diagrammatic top view of a portion of a wafer 150. The wafer 150 contains a plurality of piezoelectric micromachined ultrasonic transducers 200 that are formed on a substrate, for example a silicon substrate. The transducers 200 are arranged into a plurality of horizontal rows. Each transducer 200 is partially surrounded or encircled by a respective trench 300. The PMUT 200 is described in more detail in U.S. patent application Ser. No. 13/105,902, filed on Dec. 13, 2013, entitled "Layout and Method of Singulating Miniature Ultrasonic Transducers", the disclosure of which is hereby incorporated by reference in its entirety. According to the various aspects of the present disclosure, a protective film or layer may be coated on a front surface of the wafer 150 in a wafer-scale process. This wafer-level coating process is discussed below with reference to FIGS. 3-10.

In more detail, FIGS. 3-10 are diagrammatic fragmentary cross-sectional side views of a portion of the wafer 150. The FIGS. 3-10 each correspond to a different stage of fabrication in accordance with various aspects of the present disclosure. FIGS. 3-10 have been simplified for the sake of clarity to better understand the inventive concepts of the present disclosure. Also, since the same fabrication processes are performed to all of the ultrasonic transducers 200, the discussions below will focus on just several of the transducers 200 (for example three transducers 200 as shown in FIGS. 3-9) for purposes of simplicity and clarity.

The PMUT 200 can be included in the IVUS imaging system 100 of FIG. 1, for example in the transducer assembly 122 included in the IVUS catheter 102. The transducer 200 has a small size and provides high resolution, such that it is well suited for intravascular imaging. In some embodiments, the PMUT 200 has a size of approximately 500 microns, can operate in a frequency range between about 20 MHz and 80 MHz, and can provide better than 50 micron resolution while providing depth penetration up to 10 mm. Furthermore, the piezoelectric membrane of transducer 200 is preferably deflected to form a substantially spherical depression to create a focused aperture. The ultrasound beam is nominally focused at the center of curvature of the spherical deflection, and the ultrasound beam width in the focal zone is minimized thus providing high resolution ultrasound images. The various aspects of the ultrasound transducer 200 and its fabrication are discussed in greater detail below.

In the depicted embodiment, the ultrasound transducer 200 is a piezoelectric micromachined ultrasound transducer (PMUT). In other embodiments, the transducer 200 may include an alternative type of transducer. Additional features can be added in the ultrasound transducer 200, and some of the features described below can be replaced or eliminated for additional embodiments of the ultrasound transducer 200.

Figure 3:
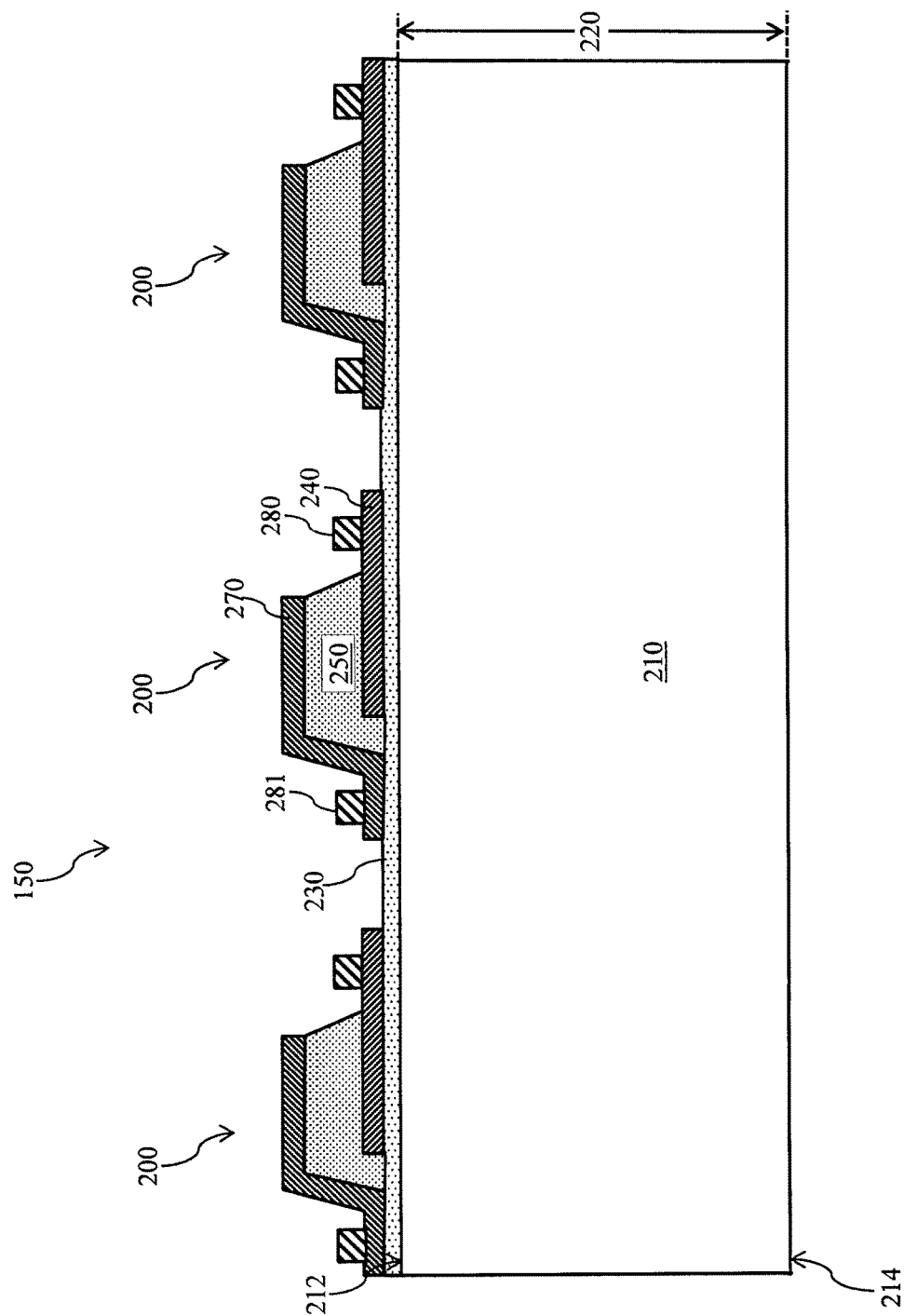
FIGS. 3-10 are diagrammatic cross-sectional side views of ultrasound transducers at different stages of fabrication according to various aspects of the present disclosure.

As shown in FIG. 3, the transducer 200 includes a substrate 210. The substrate 210 has a surface 212 and a surface 214 that is opposite the surface 212. The surface 212 may also be referred to as a front surface or a front side, and the surface 214 may also be referred to as a back surface or a back side. In the depicted embodiment, the substrate 210 is a silicon substrate. The substrate 210 may be composed of another suitable material depending on design requirements of the PMUT transducer 200 in alternative embodiments.

An initial thickness 220 of the substrate 210 is measured between the surface 212 and the surface 214. In some embodiments, the initial thickness 220 is in a range from about 200 microns (um) to about 600 um.

A dielectric layer 230 is formed over the surface 212 of the substrate 210. The dielectric layer 230 may be formed by a suitable method known in the art, such as thermal oxidation, chemical vapor deposition (CVD), physical vapor deposition (PVD), atomic layer deposition (ALD), or combinations thereof. The dielectric layer 230 may contain an oxide and/or a nitride material, for example silicon dioxide, silicon nitride, or silicon oxynitride. The dielectric layer 230 provides a support surface for the layers to be formed thereon. The dielectric layer 230 also provides electrical insulation from the underlying substrate which may be slightly conductive (in the case of silicon).

A conductive layer 240 is formed over the dielectric layer 230. The conductive layer 240 may be formed by a suitable deposition process such as evaporation, sputtering, electroplating, etc. In the illustrated embodiment, the conductive layer 240 is composed of a stack of one or more metal components. For example, the metal stack may include titanium, tungsten, chromium, gold, and/or aluminum components. The conductive layer 240 is patterned using techniques such as photolithography, with liftoff or etching used to remove unwanted portions of the conductive layer 240. For simplicity, FIG. 3 illustrates the conductive layer 240 only after it has been patterned.

A piezoelectric film 250 is formed over the dielectric layer 230 and the conductive layer 240. In various embodiments, the piezoelectric film 250 may include piezoelectric materials such as polyvinylidene difluoride (PVDF) or its co-polymers, P(VDF-TrFE) with trifluoroethylene, or P(VDF-TFE) with tetrafluoroethylene. Alternatively, polymers such as P(VDF-CTFE) or P(VDF-CFE) may be used. In the illustrated embodiment, the piezoelectric material used in the piezoelectric film 250 contains P(VDF-TrFE).

The piezoelectric film 250 is patterned to achieve a desired shape, for example the shapes shown in FIG. 3. Unwanted portions of the piezoelectric film 250 are removed in the patterning process. As a result, portions of the dielectric layer 230 and the conductive layer 240 are exposed. In the present embodiment, the piezoelectric film 250 is etched in a manner to form a chamfer to allow deposition for a top electrode to be formed. The chamfer may manifest itself as the trapezoidal sidewall shown in the cross-sectional view of FIG. 3. It is also understood that an adhesion-promoting layer (not illustrated herein) may be formed between the piezoelectric film 250 and the conductive layer 240 in some embodiments, so that the piezoelectric film 250 is more likely to stick to the conductive layer 240.

A conductive layer 270 (i.e., the top electrode) is formed over the piezoelectric film 250 using a suitable deposition process known in the art. In the illustrated embodiment, the conductive layer 270 is composed of a stack of one or more metal components. For example, the metal stack may include titanium, tungsten, chromium, gold, and/or aluminum components. The conductive layer 270 is patterned using techniques such as photolithography, with liftoff or etching used to remove unwanted portions of the conductive layer 270. For simplicity, FIG. 3 illustrates the conductive layer 270 only after it has been patterned. The conductive layers 240 and 270 and the piezoelectric layer 250 may collectively constitute a transducer membrane. Alternatively, the transducer membrane may also include the portion of the dielectric layer disposed directly beneath the conductive layers 240 and 270 and piezoelectric layer 250.

Bond pads 280-281 (also referred to as conductive contacts or pad metals) are then formed. The bond pad 280 is formed on, and electrically coupled, to the conductive layer 240, and the bond pad 281 is formed on, and electrically coupled to, the conductive layer 270. The bond pads 280-281 may be formed by depositing a layer of metal over the conductive layers 240 and 270 and thereafter patterning the layer of metal in a lithography process. As a result, the bond pads 280-281 are formed. The bond pads 280-281 may serve as electrodes for the transducer 200. Through these electrodes (i.e., the bond pads 280-281), electrical connections may be established between the transducer 200 and external devices such as electronic circuitry (not illustrated herein). The electronic circuitry can excite the transducer membrane so that it generates sound waves, particularly sound waves in an ultrasound range.

Figure 4:
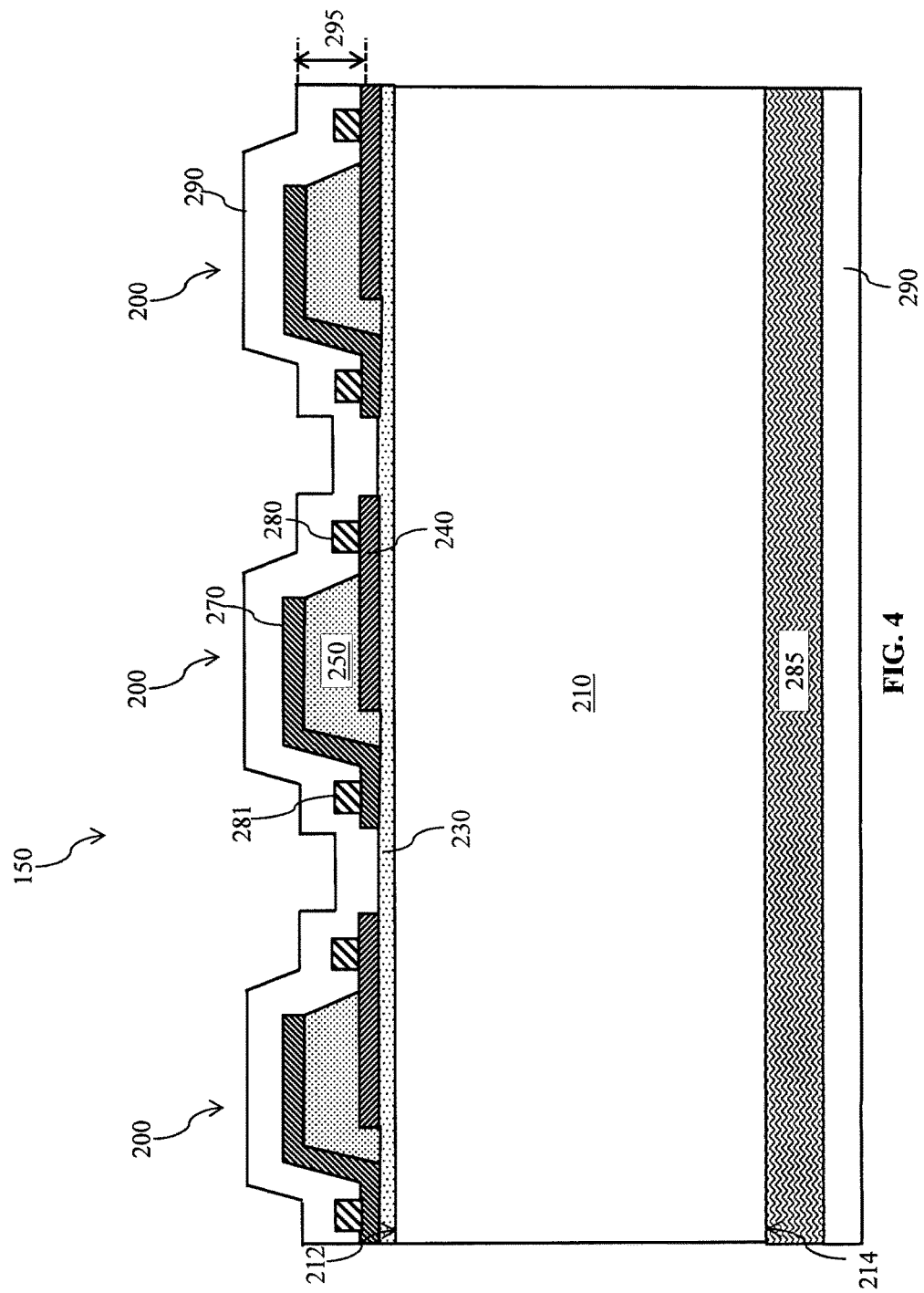

Referring now to FIG. 4, the back side 214 of the wafer 150 is covered with a material 285, which may include tape or another type of sacrificial material that can be easily removed in a later process. Thereafter, a protective layer 290 is conformally coated over the entire wafer 150. Since only a portion of the wafer 150 is illustrated in FIG. 4, the protective layer 290 is shown to be coated over the front side 212 and over the back side 214 of the wafer (i.e., the lateral edges of the wafer 150 and the protective layer 290 coated thereon are not illustrated herein), but it is understood that the coating of the protective layer 290 is done on the wafer level.

The protective layer 290 serves two purposes. First, it provides electrical insulation against fluids such as blood or saline. Second, it provides acoustic impedance matching between the membrane of transducer 200 and the surrounding medium, typically saline or blood. Therefore, the protective layer 290 herein includes a material that is electrically insulating and which exhibits an acoustic impedance intermediate between that of the transducer membrane and that of the surrounding medium (saline). In some embodiments, the protective layer 290 includes chemical vapor deposited poly(p-xylylene) polymers (hereinafter referred to in its trade name Parylene).

Conformal coating means that the protective layer 290 is coated on every surface that it can reach and with even or uniform thickness. In other words, the protective layer 290 will follow the cross-sectional profile or outline of the various components disposed over the front side 212 and the back side 214 of the wafer 150. Since the back side 214 is flat (and the material 285 is flat), the portion of the protective layer 290 formed on the material 285 in the back side 214 is also flat or has a flat surface. However, since the PMUT transducers 200 formed on the front side 212 of the wafer 150 are not co-planar with the front surface of the substrate 210, the protective layer 290 follows the rises and falls of the components of the PMUT transducers 200, for example the bond pads 280-281, the conductive layers 240 and 270, and the piezoelectric film 250. It is understood that for reasons of simplicity, the conformal coating characteristic of the protective layer 290 may not be precisely illustrated in the FIGURES herein.

The protective layer 290 has a thickness 295 that is uniform throughout. In some embodiments, the protective layer 290 has a thickness 295 which is just enough to provide electrical insulation, such as approximately 2 microns to 5 microns. In other embodiments, the protective layer 290 has a thickness 295 chosen to provide both electrical insulation and acoustic matching, in which case the thickness 295 may be approximately one-quarter of the acoustic wavelength at the transducer center frequency, such as approximately 13 microns for a transducer having a 40 MHz center frequency.

Figure 5:
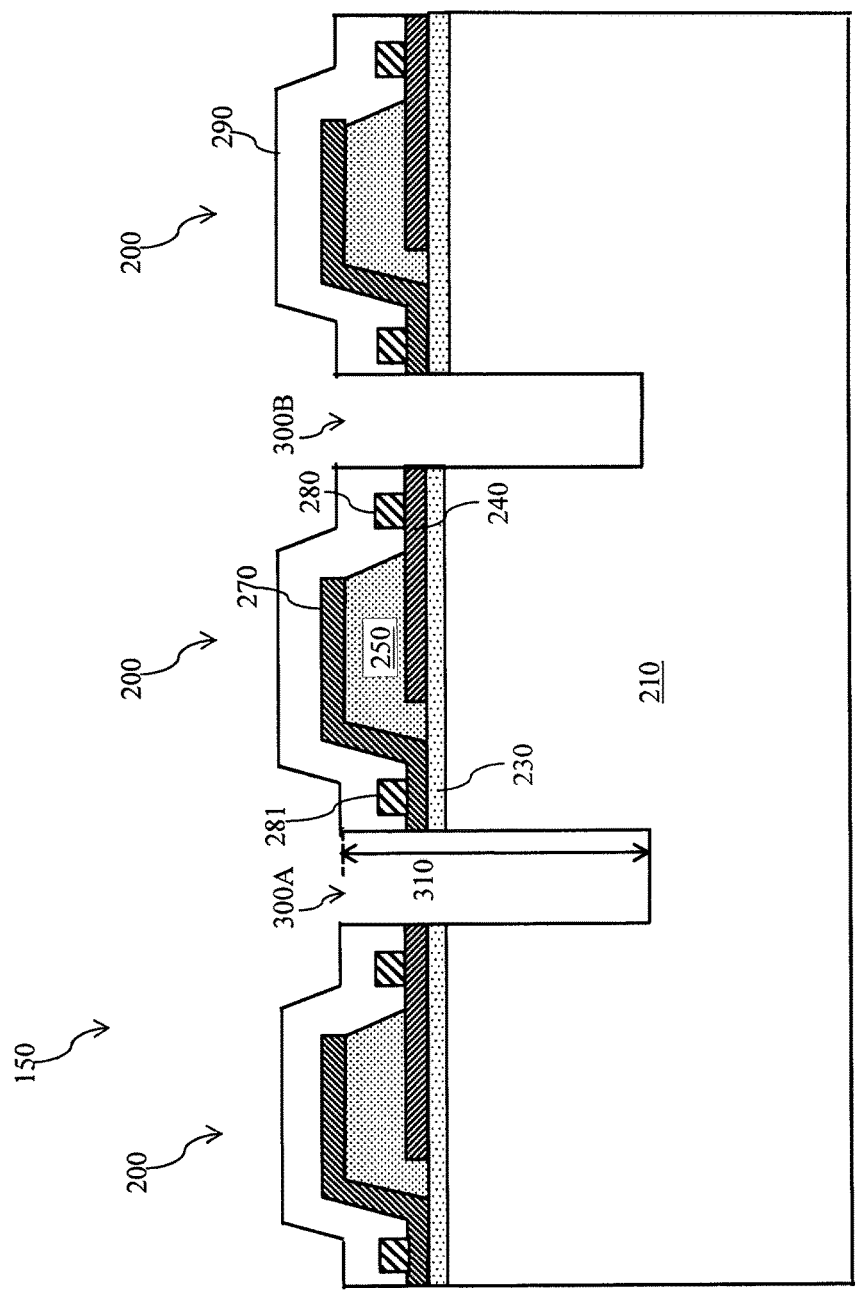

Referring now to FIG. 5, the material 285 (seen in FIG. 4) on the back side 214 of the wafer 150 has been removed, along with the protective layer 290 formed thereon. A first etching process is performed from the front side 212 to etch a plurality of trenches 300 in the substrate 210. The trenches 300 may be formed by a dry etching process, such as a deep reactive-ion etching (DRIE) process. Each of the trenches 300 partially surrounds or encircles a respective one of the transducers, for example as shown in the top view of FIG. 2. In the cross-sectional view of FIG. 2, only trenches 300A-300B are shown. It is understood that the trenches 300A and 300B are actually parts of a single continuous trench that surrounds one of the transducers 200, even though they appear as two trenches in the cross-sectional view of FIG. 5. In the present embodiments, the trenches 300 have a trench depth 310 that is in a range from about 80 um to about 100 um. Of course, the depth 310 may have different values in alternative embodiments.

It is understood that before the trenches 300 are etched, a photomask may be provided on the front side 212 to cover up portions of the protective layer 290 that should not be etched. The photomask contains openings disposed between adjacent PMUT transducers 200, and it is through these openings that the trenches 300 are etched. For reasons of simplicity, the photomask is not illustrated herein.

Figure 6:
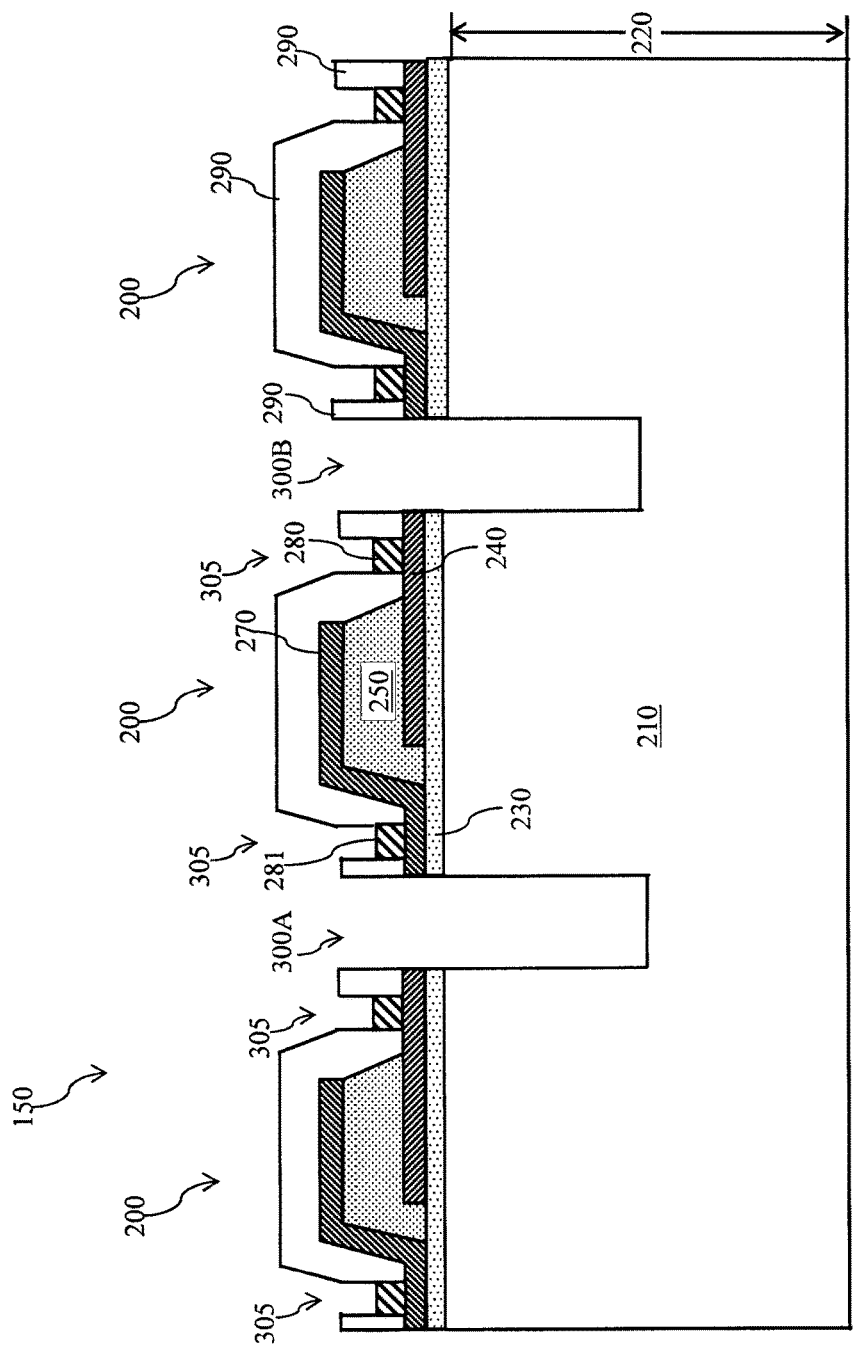

Referring now to FIG. 6, another etching process is performed to expose the bond pads 280-281 by removing portions of the protective layer 290 overlying the bond pads 280-281. The removal of the portions of the protective layer 290 forms recesses or openings 305 above each of the bond pads 280-281. Again, another photomask may first be provided over the front side 212 of the wafer before the etching process is performed, where the photomask contains openings that are vertically aligned with the bond pads 280-281. The photomask prevents the protective layer 290 disposed therebelow from being etched while allowing the portions thereof exposed by the openings in the photomask to be removed by the etching process. After the etching process is completed, the bond pads 280-281 are exposed and are ready for wire bonding.

It is understood that although the FIGS. 4-6 show the trenches 300 being formed before the recesses 305 are formed, this particular order is not important. In other words, the recesses 305 may be formed before the trenches 300 are formed in other embodiments.

Since etching is used to introduce openings (e.g., trenches 300 and recesses 305) herein, the lateral edges (e.g., sidewalls of the trenches 300 or the recesses 305) of the protective layer 290 herein would exhibit characteristics of the particular etching process used to form the opening. These characteristics are different for the various etching methods that may be employed, and different than if the openings herein were formed by a mechanical sawing process, for example.

Figure 7:
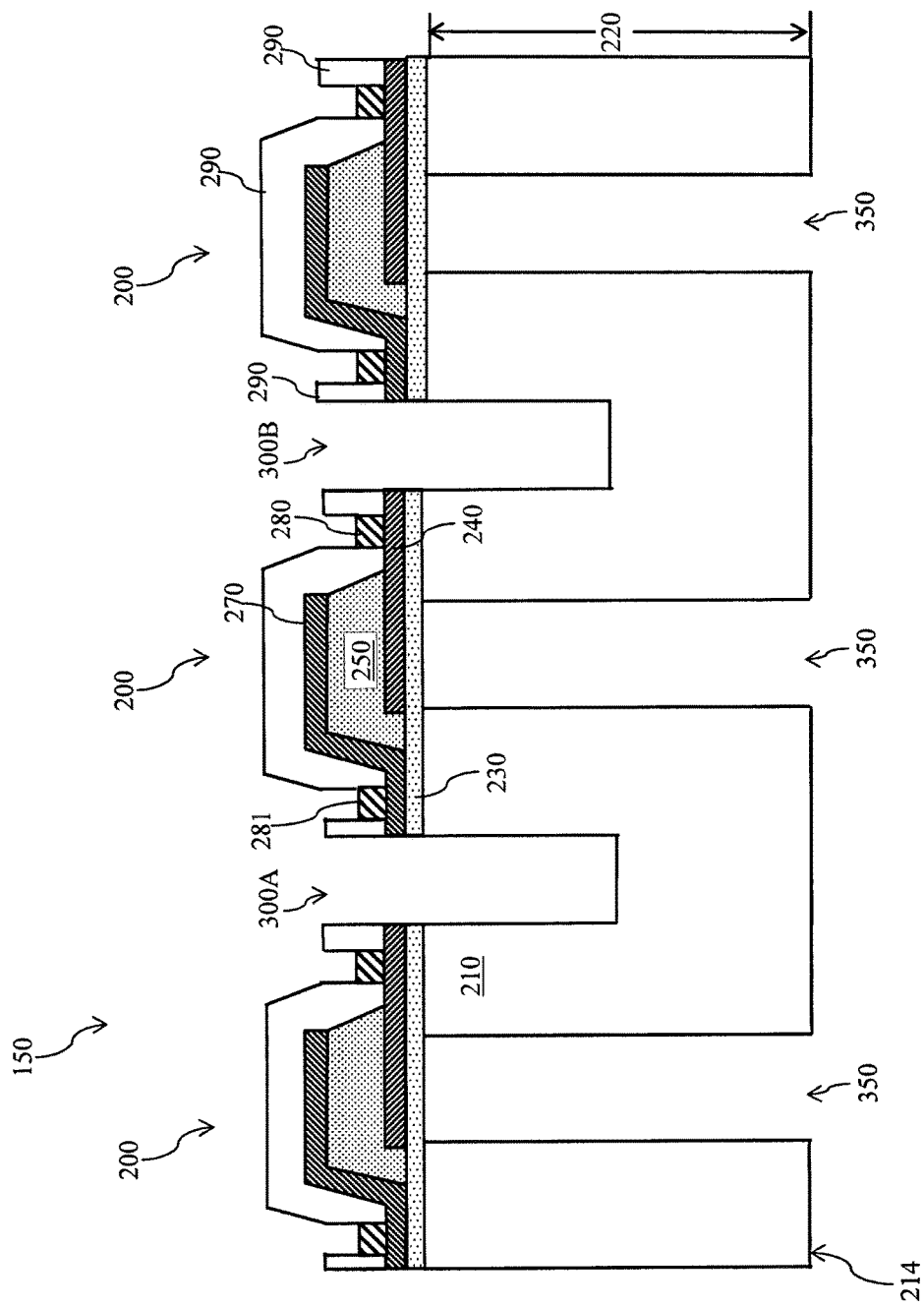

Referring now to FIG. 7, a plurality of openings 350 is formed in the substrate 210 from the back side 214. Each opening 350 is formed under (or vertically aligned with) a membrane of one of the transducers 200. The openings 350 may also be referred to as wells, voids, or recesses. The openings 350 are formed up to the dielectric layer 230 in the illustrated embodiment. In other words, a portion of the dielectric layer 230 is exposed to the back side 214 by the openings 350. However, it is understood that in other embodiments, the openings 350 may go up through the dielectric layer 230 and stop at the conductive layer 240 (i.e., bottom electrode). In some embodiments, the openings 350 are formed by an etching process, for example a deep reactive ion etching (DRIE) process. Each opening 350 corresponds to an aperture of the transducer 200.

It is understood that although the present embodiment involves forming the trenches 300 from the front side 212 before forming the openings 350 from the back side 214, these processes may be reversed in other embodiments. In other words, the openings 350 may be formed before the trenches 300 in other embodiments.

Figure 8:
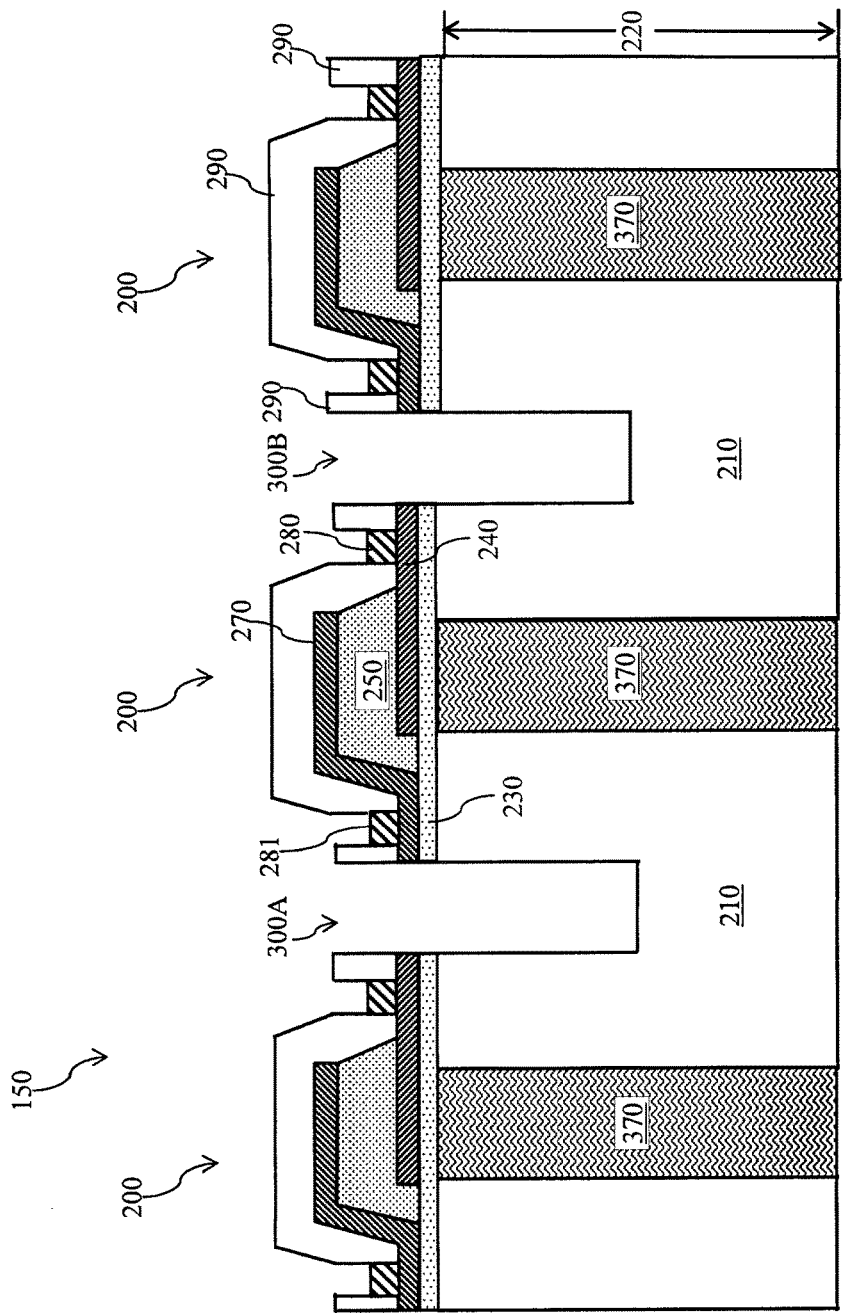
Figure 9:
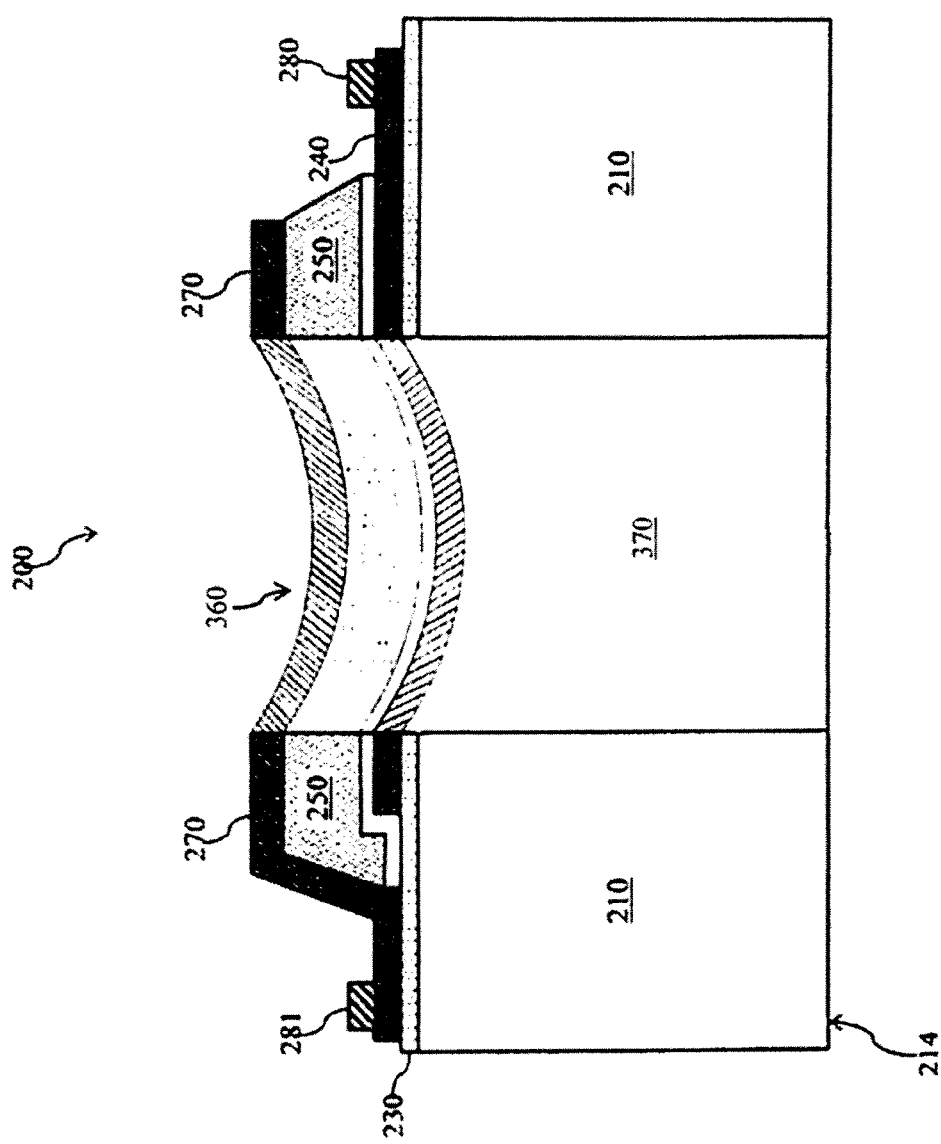

Referring now to FIG. 8, the openings 350 are filled with a backing material 370. Before the backing material 370 is cured to form a solid backing, and while the backing material remains a liquid, the membrane may be deflected to form a spherical bowl-shaped curvature in order to create a focused transducer aperture. For simplicity, the deflection process is not depicted in FIG. 8. Once the backing material 370 has cured, the backing material 370 filling the opening 350 retains the membrane deflection and it also acts to deaden any the sound waves emerging from the back of the piezoelectric film 250 into the backing material 370. In more detail, the backing material 370 physically contacts the bottom surface (or back side surface) of the dielectric layer 230 (or the back surface of the conductive layer 240 in embodiments where the dielectric layer 230 has been removed in the opening 350). Therefore, one function of the backing material 370 is that it helps lock the transducer membrane 360 into place such that its shape (for example an arcuate shape) is maintained. The backing material 370 also contains an acoustically attenuative material that can absorb sound waves generated by the transducer membrane 360 that propagate into the backing material 370. Such sound waves (or acoustic energy) include waves reflected from structures and interfaces of a transducer assembly, for example when the ultrasound transducer 200 is included in the transducer assembly 122 of FIG. 1.

The layers disposed over the opening 350 (i.e., the transducer membrane) are also deflected to form a concave surface. Stated differently, the portion of the dielectric layer 230 exposed by the opening 350 as well as the portions of the transducer membrane disposed over the portion of the dielectric layer 230 are bent toward the back side 214. Therefore, an arcuate-shaped transducer membrane 360 is formed. For the sake of simplicity, the arcuate-shaped transducer membrane is not illustrated for all the transducers 200 of FIG. 5, but it is understood that each transducer 200 may be shaped as (or similar to) the transducer 200 shown in FIG. 9. Additional details of shaping the transducer membrane are disclosed in Provisional U.S. Patent Application 61/745,344, titled "Method and Apparatus For Shaping Transducer Membrane" to Dylan Van Hoven, filed on Dec. 21, 2012, the contents of which are hereby incorporated by reference in its entirety.

Figure 10:
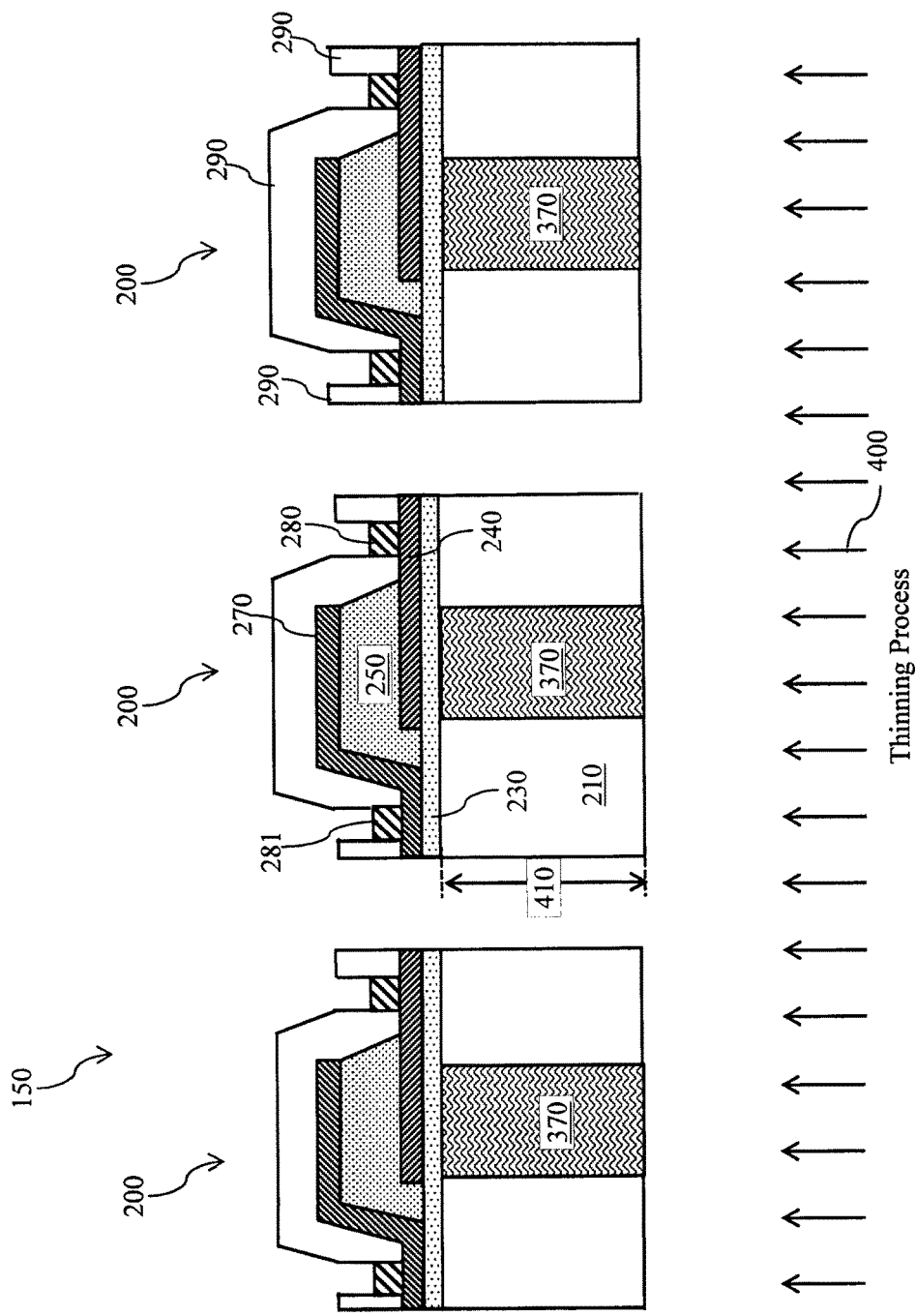

Referring now to FIG. 10, a thinning process 400 is performed from the back side 214 to reduce the thickness of the substrate 210. In some embodiments, a grinding, polishing, or etching process or combinations thereof may be used to remove portions of the substrate 210 (and the backing material 370 in embodiments where applicable) from the back side 214. The thinning process 400 is performed until the substrate 210 reaches a desired thickness 410. The thickness 410 is no greater than the depth 310 of the trenches 300 (shown in FIG. 5). In some embodiments, the thickness 410 of the substrate 210 after the thinning process 400 is performed is less than about 80 um, for example about 75 um.

The conformal wafer level coating of the protective layer 290 according to the various aspects of the present disclosure offers advantages. It is understood, however, that different embodiments may offer different advantages, not all advantages are necessarily discussed herein, and that no particular advantage is required for all embodiments. One advantage is that the wafer level coating is easier to perform and takes less time. In the traditional PMUT transducer fabrication process, a protective coating (e.g., a Parylene coating) is applied after the transducers are singulated and individual tadpole assemblies are formed. This is inconvenient, as it is complicated and time-consuming to introduce a large number of tadpole transducer assemblies into a Parylene (or similar) coating chamber and to protect the attached quad cables from being coated. In comparison, the wafer level coating discussed herein is performed on the wafer level, simultaneously coating thousands of transducers in one simple step, before singulation takes place.

Another advantage is that the etching process described herein reduces the likelihood of the protective coating being peeled off. According to conventional coating methods, the protective material is applied on all surfaces of the transducer assembly, including its back surfaces. This causes a problem, as sound that travels to the back of the transducer will bounce off of the protective layer covering the back side of the transducer. To alleviate this problem, certain approaches have been employed where an adhesive masking material may be applied to the back side of the transducer first, and after the coating of the protective layer on the front and back surfaces, a cutting device such as a razor blade may be used to slice off the adhesive masking material along with the protective layer formed thereon. This is a painstaking process. Furthermore, the commonly-used material (Parylene) for the protective layer has excellent adhesive properties with respect to itself, but not so much to other materials. The protective layer being cut off over the back side introduces cut edges of the protective layer, which are prone to peeling, especially if stress is applied to them. For example, the cutting process itself may introduce stress, which may inadvertently initiate the process of the protective layer being peeled off. In contrast, the edges of the protective layer herein may be defined by an etching process such as reactive ion etching. This dry etching process occurs at a molecular scale, and introduces minimal stress to the protective layer, thereby reducing the likelihood of the protective layer peeling.

Another advantage is the etching processes herein reduces the likelihood of the protective coating being peeled off. According to conventional coating methods, the protective material is applied on all surfaces of the transducer assembly, including its back surfaces. This causes a problem, as sound that travels to the back of the transducer will bounce off of the protective layer covering the back side of the transducer. To solve this problem, certain approaches have been employed where an adhesive material may be formed on the back side of the transducer first, and after the coating of the protective layer on the front and back surfaces, a cutting device such as a razor blade may be used to slice off the adhesive material along with the protective layer formed thereon. This is a painstaking process. Furthermore, the commonly-used material (Parylene) for the protective layer has better adhesive properties with respect to itself, but not so much to other materials. The protective layer being cut off over the back side may introduce cut edges of the protective layer, which are prone to peeling, especially if stress is applied to them. For example, the cutting process itself may introduce stress, which may inadvertently initiate the process of the protective layer being peeled off. In comparison, the edges of the protective layer herein may be defined by an etching process such as reactive ion etching. The dry etching process occurs at a molecular scale, which introduces minimal stress to the protective layer, thereby reducing the likelihood of the protective layer peeling.

Another advantage of the wafer level application of the protective layer 290 is that it encapsulates the edges of the underlying layers, helping to prevent peeling of those underlying layers during the later stages of transducer fabrication and assembly. For example, the edges of the conductive layers 240 and 270 may be subject to peeling if they are not strongly bonded to the surrounding layers. Similarly, the piezoelectric film 250 may be subject to peeling as well. Peeling may be initiated by stresses encountered during the later stages of transducer fabrication due to thermal processes, membrane deflection, or device handling. The presence of the protective layer 290 according to the present invention, encapsulating the edges of the underlying layers will help to prevent peeling of those layers.

Figure 11:
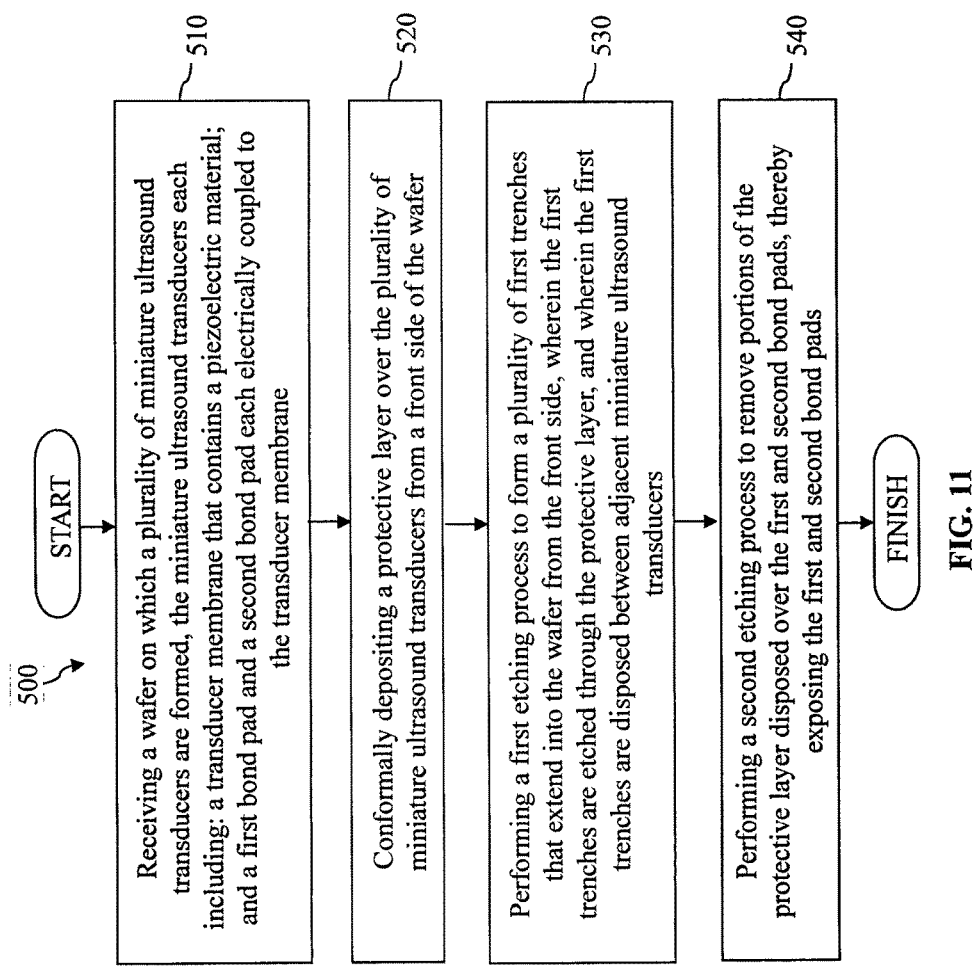
FIG. 11 is a flowchart of a method of performing a wafer level coating of a protective layer on transducers according to various aspects of the present disclosure.

FIG. 11 is a flowchart of a method 500 of fabricating miniature ultrasound transducers. The method 500 includes a step 510 of receiving a wafer on which a plurality of miniature ultrasound transducers is formed. The miniature ultrasound transducers each include a transducer membrane that contains a piezoelectric material, a first bond pad, and a second bond pad, each electrically coupled to the transducer membrane. In some embodiments, the piezoelectric material includes a polymer polyvinylidene difluoride (PVDF), a copolymer of vinylidene difluoride with trifluoroethylene designated P(VDF-TrFE), or a copolymer of vinylidene difluoride with tetrafluoroethylene designated P(VDF-TFE).

The method 500 includes a step 520 of conformally depositing a protective layer over the plurality of miniature ultrasound transducers from a front side of the wafer. In some embodiments, the protective layer contains a Parylene material. In some embodiments, the protective layer is deposited in a chemical vapor deposition process.

The method 500 includes a step 530 of performing a first etching process to form a plurality of first trenches that extend into the wafer from the front side, wherein the first trenches are etched through the protective layer and deeply into the substrate, and wherein the first trenches are disposed between adjacent miniature ultrasound transducers. In some embodiments, the first etching process includes a deep reactive-ion etching (DRIE) process.

The method 500 includes a step 540 of performing a second etching process to remove portions of the protective layer disposed over the first and second bond pads, thereby exposing the first and second bond pads.

It is understood that additional fabrication steps may be performed before, during, or after the steps 510-540 to complete the fabrication of the transducer. For example, the method 500 may include a step of covering the back side of the wafer before the step 520 of conformally depositing of the protective layer. In some embodiments, the method 500 may further include the following steps: etching a plurality of second trenches from the back side of the wafer, wherein the second trenches are each aligned with a respective one of the transducer membranes; filling each of the second trenches with a backing material such as epoxy and deflecting the transducer membrane prior to epoxy cure; and thinning the wafer from the back side. Other fabrication steps may also performed, but these additional fabrication steps are not discussed herein for reasons of simplicity.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A miniature ultrasonic transducer, comprising:
   a substrate having a first side and a second side opposite the first side;
   a well disposed in the substrate, the well being filled with a backing material;
   a transducer membrane disposed over the first side of the substrate and over the well, the transducer membrane containing a piezoelectric layer;
   a first conductive layer disposed over the transducer membrane;
   a second conductive layer disposed beneath the transducer membrane;
   a first bond pad disposed over and in contact with the first conductive layer on the first side of the substrate; and a second bond pad disposed over and in contact with the second conductive layer on the first side of the substrate; and a protective layer conformally disposed over and in contact with the transducer membrane, the first conductive layer, and the second conductive layer, but not over the second side of the substrate, the first bond pad, or the second bond pad.

2. The miniature ultrasonic transducer of claim 1, wherein the protective layer contains a material that is electrically insulating and exhibits an acoustic impedance that is intermediate between an acoustic impedance of the transducer membrane and an acoustic impedance of a medium surrounding the miniature ultrasonic transducer.

3. The miniature ultrasonic transducer of claim 1, wherein the protective layer contains Parylene.

4. The miniature ultrasonic transducer of claim 1, wherein the protective layer has a thickness that is approximately one-quarter of an acoustic wavelength at a nominal center frequency of the transducer.

5. The miniature ultrasonic transducer of claim 1, wherein a sidewall of the protective layer is co-planar with a sidewall of the substrate.

6. The miniature ultrasonic transducer of claim 1, wherein the backing material contains epoxy.

7. The miniature ultrasonic transducer of claim 1, wherein the piezoelectric layer contains polyvinylidene difluoride (PVDF), poly(vinylidene difluoride-trifluoroethylene) (P(VDF-TrFE)), or poly(vinylidene fluoride-tetrafluoroethylene) (P(VDF-TFE)).

8. A miniature ultrasonic transducer, comprising:
a substrate having a first side and a second side opposite the first side;
a well disposed in the substrate, the well being filled with a backing material;
a transducer membrane disposed over the first side of the substrate and over the well, the transducer membrane containing a piezoelectric layer;
a first conductive layer disposed over the transducer membrane;
a second conductive layer disposed below the transducer membrane;
a first bond pad disposed on the first conductive layer;
a second bond pad disposed on the second conductive layer; and
a protective layer disposed over the transducer membrane and over the first and second conductive layers, wherein the protective layer contains recesses that expose the first and second bond pads.

9. The miniature ultrasonic transducer of claim 8, wherein the protective layer is disposed over the transducer membrane and over the first and second conductive layers in a conformal manner.

10. The miniature ultrasonic transducer of claim 8, wherein the protective layer contains a material that is electrically insulating and exhibits an acoustic impedance that is intermediate between an acoustic impedance of the transducer membrane and an acoustic impedance of a medium surrounding the miniature ultrasonic transducer.

11. The miniature ultrasonic transducer of claim 8, wherein the protective layer has a thickness that is approximately one-quarter of an acoustic wavelength at a nominal center frequency of the transducer.

12. The miniature ultrasonic transducer of claim 8, wherein:
the piezoelectric layer contains polyvinylidene difluoride (PVDF), poly(vinylidene difluoride-trifluoroethylene) (P(VDF-TrFE)), or poly(vinylidene fluoride-tetrafluoroethylene) (P(VDF-TFE));
the backing material contains epoxy; and
the protective layer contains Parylene.

13. A method of fabricating miniature ultrasound transducers, the method comprising:
receiving a wafer on which a plurality of miniature ultrasound transducers are formed, the miniature ultrasound transducers each including:
over a front side of the wafer, a transducer membrane that contains a piezoelectric material;
a first conductive layer disposed over the transducer membrane;
a second conductive layer disposed below the transducer membrane; and
a first bond pad and a second bond pad each electrically coupled to the transducer membrane via the first and second conductive layers, respectively, wherein the first bond pad is disposed over and in contact with the first conductive layer and the second bond pad is disposed over and in contact with the second conductive layer;
covering a back side of the wafer with a sacrificial layer;
conformally depositing a protective layer over the wafer;
performing a first etching process to form a plurality of first trenches that extend into the wafer from the front side, wherein the first trenches are etched through the protective layer, and
wherein the first trenches are disposed between adjacent miniature ultrasound transducers;
performing a second etching process to remove portions of the protective layer disposed over the first and second bond pads, thereby exposing the first and second bond pads; and
removing the sacrificial layer from the back side of the wafer.

14. The method of claim 13, further comprising:
etching a plurality of second trenches from the back side of the wafer, wherein the second trenches are each aligned with a respective one of the transducer membranes;
filling each of the second trenches with a backing material; and
thinning the wafer from the back side.

15. The method of claim 14, wherein the filling the second trenches comprises filling the second trenches with epoxy.

16. The method of claim 13, wherein the conformally depositing the protective layer comprises depositing a parylene material as the protective layer.

17. The method of claim 13, wherein the conformally depositing the protective layer comprises a chemical vapor deposition process.

18. The method of claim 13, wherein the first etching process comprises a deep reactive-ion etching process.

19. The method of claim 13, wherein the piezoelectric layer contains polyvinylidene difluoride (PVDF), poly(vinylidene difluoride-trifluoroethylene) (P(VDF-TrFE)), or poly(vinylidene fluoride-tetrafluoroethylene) (P(VDF-TFE)).

* * * * *